United States Patent [19]

Bansleben et al.

[11] Patent Number: 5,017,306

[45] Date of Patent: May 21, 1991

[54] CORROSION INHIBITOR

[75] Inventors: Donald A. Bansleben, Columbia; Charles G. Carter, Silver Spring; Ranjit Kumar, Columbia, all of Md.

[73] Assignee: W. R. Grace & Co.-Conn., New York, N.Y.

[21] Appl. No.: 269,209

[22] Filed: Nov. 9, 1988

[51] Int. Cl.$^5$ .............................................. C07F 9/09
[52] U.S. Cl. .................................. 252/389.23; 562/20
[58] Field of Search ................... 252/389.22, 389.23, 252/180; 562/20, 23; 558/105, 89

[56] References Cited

U.S. PATENT DOCUMENTS

| | | | |
|---|---|---|---|
| 2,535,172 | 12/1950 | Tawney | 558/87 |
| 2,632,767 | 3/1953 | Smith et al. | 558/164 |
| 2,900,408 | 8/1959 | Blaser et al. | 558/136 |
| 3,032,578 | 5/1962 | MacMullen et al. | 558/186 |
| 3,105,436 | 5/1970 | Silverstein et al. | 252/389.2 |
| 3,341,467 | 9/1967 | Hwa | 252/389.23 X |
| 3,429,824 | 2/1969 | Tate | 252/8.552 X |
| 3,488,289 | 1/1970 | Tate | 252/8.552 X |
| 3,532,639 | 10/1970 | Hatch | 252/389.22 |
| 3,600,470 | 8/1971 | Lewis . | |
| 3,714,066 | 1/1973 | King et al. | 252/389.23 |
| 3,738,806 | 6/1973 | Feiler | 252/389.22 X |
| 3,803,047 | 4/1974 | Hwa | 252/389.22 |
| 3,803,048 | 4/1974 | Hwa | 252/389.22 |
| 3,837,803 | 9/1974 | Carter et al. | 252/389.2 X |
| 3,890,228 | 6/1975 | Hwa et al. | 210/699 |
| 3,960,576 | 6/1976 | Carter et al. | 389/22 |
| 3,970,729 | 7/1976 | Walsh et al. | 549/529 |
| 4,003,842 | 1/1977 | Suen et al. | 252/387 X |
| 4,029,696 | 6/1977 | Sommer et al. | 252/186.43 X |
| 4,052,160 | 10/1977 | Cook et al. | 252/389.23 X |
| 4,056,480 | 11/1977 | Herber | 252/78.5 |
| 4,069,247 | 1/1978 | Kleiner | 562/8 |
| 4,085,134 | 4/1978 | Redmore et al. | 562/14 |
| 4,092,244 | 5/1978 | Suen et al. | 252/387 X |
| 4,206,075 | 6/1980 | Boffardi | 252/389.22 |
| 4,209,487 | 6/1980 | Hogue et al. | 252/389.22 X |
| 4,212,832 | 7/1980 | Mitschke et al. | 558/87 |
| 4,276,089 | 6/1981 | Moran | 252/389.22 X |
| 4,416,830 | 11/1983 | Morr et al. | 558/165 |
| 4,440,646 | 4/1974 | Budnick | 210/699 |
| 4,465,516 | 8/1984 | Danner et al. | 252/389.2 |
| 4,717,542 | 1/1988 | Mitchell | 252/389.23 X |
| 4,719,031 | 1/1988 | Coleman | 252/180 |

FOREIGN PATENT DOCUMENTS

| | | |
|---|---|---|
| 535946 | 1/1957 | Canada . |
| 1076244 | 7/1967 | United Kingdom . |
| 2112370A | 7/1983 | United Kingdom . |

OTHER PUBLICATIONS

J. S. Amato et al., "A New Preparation of Chloromethyl Methyl Ether Free of Bis(Chloromethyl) Ether", Synthesis 970-971 (1979).
T. H. Chan et al., "Unexpected Site Selectivity of Halotrimethylsilane with 2,5-Dimethoxytetrahydrofuran and 2,6-Dimethoxytetrahydropyran", Tet Lett. 24, 1225-1228 (1983).
Griffiths et al., "The Reaction of Phosphorus Trichloride and Paraformaldehyde", Phosphorous, 6, 223-230 (1976).
K. A. Petrov et al., "Synthesis and Properties of (Substituted Methyl) Phosphonates", Zhur. Obschchei. Khim. 12 2741-2749 (1977) (1978 Translation Plenum Publishing Corp., 2494-2501).
D. P. Phillion et al., "Synthesis and Reactivity of Diethyl Phosphonomethyltriflate", Tet. Lett. 27 1477-1480 (1986).
D. Redmore, "Heterocuclic Systems Bearing Phosphorus Substituents, Synthesis and Chemistry", Chem. Rev., 71, 315-337 (1971) and Table III.
L. Maier et al., "Organic Phosphorus Compounds, 70, Preparation and Properties of New Phosphorus Containing Chelating Agents for Calcium and Magnesium Ions", Phosphorous and Sulfur, 5, 45-51 (1978).
Chem. Abstracts, vol. 96, entry 183846E (1981); Stulli et al.: "Effect of Complexing Agents on the Properties of Synthetic Cutting Fluids", Khim. Tekhnol. Topl. Masel.
Chem. Abstracts, vol. 95, entry 61756j (1981)–Jupe et al., "Polyhydric", Phenols Ger. Offen., 2,942,366.
D. A. Nicholson et al., "A Convenient Method of Esterfication of Polyphosphonic Acids", Journal of Organic Chemistry, 35, 3149-3150 (1970).
Chemical Abstracts, vol. 37, Cols. 3048-3049 (1943), V. S. Abramov et al., "Action of Dibromomethyl and (List continued on next page.)

Primary Examiner—Robert L. Stoll
Assistant Examiner—Valerie D. Fee
Attorney, Agent, or Firm—James P. Barr

[57] ABSTRACT

A method of preparing phosphonate compositions comprising di-(phosphonomethyl) formal is disclosed which comprises (a) forming an intimate mixture of hydroxymethylphosphonic acid and formaldehyde or its condensates, said mixture having a least about 0.5 equivalents of formaldehyde per equivalent of hydroxymethylphosphonic acid; and (b) subjecting said intimate mixture to a temperature of between about 100° C. and 180° C. for a time sufficient to allow the components to react to form a reacted mixture comprising di-(phosphonomethyl) formal. Di-(phosphonomethyl) formal, phosphonate compositions wherein at least about 20 more % of the phosphonate groups are present as di-(phosphonomethyl) formal, and phosphonate compositions which comprise hydroxymethylphosphonic acid and di-(phosphonomethyl) formal such that the mole ratio of phosphonate groups present as di-(phosphonomethyl) formal to phosphonate groups present as hydroxymethylphosphonate is at least about 1:3, as disclosed, may be used for corrosion inhibition in aqueous systems.

23 Claims, No Drawings

OTHER PUBLICATIONS

Dichloromethyl Ethers on Ethyl Phosphite and Sodium Diethyl Phosphite".

Chemical Abstracts, vol. 55, Col. 6367 (1961), K. A. Petrov et al., "Diphosphonates, III, Synthesis of O- and S-Diphosphonates", Zhur. Obshchei Khim., 30, 1960–1964 (1960).

Chemical Abstracts, vol. 56, Cols. 11418–11419 (1962), W. Treibs et al., "Autooxidation in the Presence of Alcohols and Protons III, Autooxidation of Cyclenes, Hydroarenes, and Hydroheterocycles", Chem. Ber. 94, 2983–2989 (1961).

Chemical Abstracts, vol. 58, Cols. 6866–6868 (1963), S. Julia et al., "Synthesis of Substituted—and—Chclohomocitrals and the Corresponding Ketones and Alcohols", Bull. Soc. Chim. Grance, 1952–1959 (1962).

Stauffer Chemical Company, Flame Retardant Chemical Product Data–Hydroxymethyl Phosphonic Acid.

Stauffer Chemical Company, Material Safety Data Sheet, Hydroxymethylphosphonic Acid.

CORROSION INHIBITOR

FIELD OF THE INVENTION

This invention relates to a novel class of phosphonate-containing compositions useful in water treatment, and more particularly to phosphonate compositions comprising di-(phosphonomethyl) formal and to the preparation of phosphonate compositions comprising di-(phosphonomethyl) formal.

BACKGROUND OF THE INVENTION

Much recent research has concerned development of organic corrosion inhibitors which can reduce reliance on the traditional inorganic inhibitors. Among the organic inhibitors successfully employed are numerous organic phosphonates. These compounds may generally be used without detrimental interference from other conventional water treatment additives. Phosphonic acid compounds have also been used in other fields for such purposes as flame retardants, plasticizers, lubricants, and surfactants.

It has long been known that an aqueous suspension of paraformaldehyde may be reacted with phosphorous trichloride or orthophosphorous acid to produce hydroxymethylphosphonic acid. Hydroxymethylphosphonic acid has been reported as useful in combination with zinc for corrosion control. It is also reportedly useful as an intermediate for the production of polyoxymethylene phosphonates which have utility as urethane foam flame proofers and plasticizers.

U.S. Pat. No. 3,970,729 discloses that phosphorous acid can be contacted with formaldehyde, or a formaldehyde condensate such as trioxane (a cyclic trimer of formaldehyde) or paraformaldehyde, (a linear polymer of formaldehyde) to yield a hydroxymethylphosphonic acid intermediate that can then be contacted with certain alkylene oxides to yield di-polyoxyalkylene hydroxymethylphosphonates. These products are reportedly useful as stabilizers for polyester film, plasticizers, flame retardants, lubricants and hydraulic fluids.

SUMMARY OF THE INVENTION

This invention relates to a novel class of phosphonate compositions having a substantial proportion of the phosphonate present as di-(phosphonomethyl) formal. We have found that hydroxymethylphosphonic acid can be reacted with formaldehyde at elevated temperatures to produce compositions comprising (phosphonomethyl) formal. The reaction has been found reversible, particularly under acidic aqueous is considered to compete with other reactions multiple molecules of hydroxymethylphosphonic acid conditions where the formaldehyde is not we with the hydroxymethylphosphonic acid. Accord the production of phosphonate compositions having a substantial proportion of the phosphonate present as formal is preferably facilitated b intimately mixing the hydroxymethylphosphonic with the formaldehyde before they are subjected to the reaction temperature for sufficient time to form reacted mixture comprising di-(phosphonomethyl) by providing substantially anhydrous reaction con by adding base to solutions of the di-(phosphonomethyl) formal-containing reaction products, and/or by excess formaldehyde. We have also found that the hydromexymethylphosphonic acid reactant may be produced in situ by adding phosphorous acid along with additional formaldehyde. In another aspect of this invention compositions comprising both di-(phosphonomethyl) formal and hydroxymethylphosphonic acid may be enriched in the relative amount of di-(phosphonomethyl) formal by adding sodium hydroxide and separating crystals comprising the disodium salt of hydroxymethyl phosphonic acid. The di-(phosphonomethyl) formal-containing phosphonate compositions of this invention are useful as corrosion inhibitors for aqueous systems.

It is an object of this invention to provide new and useful phosphonate-containing compositions.

It is another object of this invention to provide a novel method of preparing certain phosphonate compositions.

These and other objects of this invention will become apparent from the detailed description which follows.

DETAILED DESCRIPTION OF THE INVENTION

We have found that hydroxymethylphosphonic acid can be reacted with formaldehyde to produce compositions comprising di-(phosphonomethyl) formal according to the following reaction:

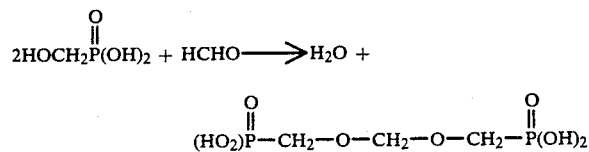

The reaction is temperature-dependent with regard to the rate of di-(phosphonomethyl) formal formation; and formaldehyde condensates such as trioxane and paraformaldehyde may also be used as formaldehyde sources for the reaction. The method of preparing phosphonate compositions in accordance with this invention thus involves subjecting a mixture of a first component consisting of hydroxymethylphosphonic acid and a second component selected from the group consisting of formaldehyde and formaldehyde polymers to a suitable reaction temperature for a time sufficient to allow the first and second components to react to form a reacted mixture comprising di-(phosphonomethyl) formal. Generally, suitable reaction temperatures are within the range of between about 100° C. to 180° C., with temperatures between about 120° C. and 150° C. being generally preferred.

The reaction may be accomplished under aqueous conditions by dissolving the hydroxymethylphosphonic acid component and the formaldehyde component in water and heating to a suitable reaction temperature. However, the reaction has been found to be reversible, and the reverse reaction of di-(phosphonomethyl) formal to hydroxymethylphosphonic acid is considered to be encouraged by acidic conditions, particularly where the di-(phosphonomethyl) formal is in solution. Accordingly, when storage as an aqueous solution is anticipated, we prefer to add base, preferably alkali metal hydroxides such as sodium hydroxide or potassium hydroxide to aqueous solutions of the di-(phosphonomethyl) formal as necessary to provide a pH of at least about 7.

We have also found however that under aqueous conditions, in addition to di-(phosphonomethyl) formal other condensates of formaldehyde and hydroxymethylphosphonic acid also tend to be produced, and thus the yields of di-(phosphonomethyl) formal are highly variable. Therefore we prefer to perform the reaction under substantially anhydrous reaction conditions. Accordingly, while some water is provided as a reaction by-product, we prefer not to add any additional water to the reaction mixture. In this procedure the formaldehyde component and hydroxymethylphosphonic acid component are mixed together in solid form, and then heated sufficiently to melt the reactants. The reaction is preferably conducted under an atmosphere of inert gas such as nitrogen or argon and/or in a closed system so that the desired substantially anhydrous conditions are maintained.

The formation of di-(phosphonomethyl) formal is considered to be inhibited by competing reactions involving multiple molecules of hydroxymethylphosphonic acid, particularly under conditions where the hydroxymethylphosphonic acid is not well mixed with formaldehyde. Accordingly, the hydroxymethylphosphonic acid and the formaldehyde are preferably mixed intimately prior to allowing formation of the desired reaction product. Intimate mixing of course results from dissolving the components in water. However, where solid mixtures are desired, mechanical blending procedures such as grinding are employed. The components are preferably mixed at a temperature below about 80° C., most preferably below about 50° C.

As noted above, the reaction has been found to be reversible, and the products resulting from the reaction, unless separated, will normally contain a mixture comprising both di-(phosphonomethyl) formal and hydroxymethylphosphonic acid. In some circumstances excess formaldehyde may be added to increase the yield of di-(phosphonomethyl) formal. However, we have also found that an aqueous solution comprising phosphonate compositions produced by reacting formaldehyde or a formaldehyde condensate with hydroxymethylphosphonic acid can generally be enriched in the proportion of di-(phosphonomethyl) formal present relative to the hydroxymethylphosphonic acid therein by adding a sufficient amount of basic sodium salt, such as sodium hydroxide, to form the disodium salt of the hydroxymethylphosphonic acid and the tetrasodium salt of the (phosphonomethyl) formal. We have found that this causes the selective formation of crystals comprising the disodium salt of hydroxymethylphosphonic acid, which can then be separated from the supernatant. The phosphonate composition of the supernatant will thus be enriched with regard to the relative amount of phosphonate present as di-(phosphonomethyl) formal.

There also appear to be other side reactions involving polycondensates of formaldehyde. However the resulting products do not appear to affect the yield of di-(phosphonomethyl) formal to the same extent as reactions involving multiple molecules of hydroxymethylphosphonic acid. While the mechanism of these competing reactions is not completely understood, it is possible that the polycondensates of formaldehyde are relatively unstable and tend to decompose during formation of the di-(phosphonomethyl) formal.

In another aspect of this invention, we have found that hydroxymethylphosphonic acid can be produced in situ from phosphorous acid and formaldehyde. This can be accomplished by mixing the phosphonic acid with at least one compound selected from the group consisting of formaldehyde and formaldehyde polymers and heating them to a temperature of between about 100° C. and 180° C. to form hydroxymethylphosphonic acid. The hydroxymethylphosphonic acid formed in this manner can in turn react with additional formaldehyde to produce di-(phosphonomethyl) formal.

We prefer to employ at least about 0.5 equivalents of formaldehyde in the starting mixture per equivalent of hydroxymethylphosphonic acid, most preferably at least about 1.0 equivalents of formaldehyde per equivalent of hydroxymethylphosphonic acid therein. In calculating the number of equivalents of formaldehyde employed each repeat unit of a formaldehyde condensate is considered to represent one equivalent of formaldehyde. For example one mole of trioxane would provide three equivalents of formaldehyde. It is noted that when hydroxymethylphosphonic acid is added to the formaldehyde component to provide the starting mixture, 0.5 equivalents of formaldehyde per equivalent of hydroxymethylphosphonic acid in the starting mixture is the stoichiometric amount for complete reaction. However, when phosphorous acid is added to the formaldehyde component to form hydroxymethylphosphonic acid in situ, additional formaldehyde is consumed as hydroxymethylphosphonic acid is formed. It is noted that stoichiometrically one equivalent of formaldehyde is required to form each equivalent of hydroxymethylphosphonic acid from phosphorous acid and that therefore a total of 3 equivalents of formaldehyde are required to form one equivalent of di-(phosphonomethyl) formal from two equivalents of phosphorous acid. While the reaction to form di-(phosphonomethyl) formal will generally not be complete, and some of the hydroxymethylphosphonic acid formed in situ may be consumed as additional hydroxymethylphosphonic acid is formed from phosphorous acid, we nevertheless prefer to use a total of about 1.5 equivalents or more of formaldehyde per equivalent of phosphorous acid so that at least about 0.5 equivalents of formaldehyde per equivalent of hydroxymethylphosphonic acid will be available during the reaction. In effect, therefore, we consider 0.5 equivalents of formaldehyde per equivalent of hydroxymethylphosphonic acid to be the same as 1.5 equivalents of formaldehyde per equivalent of phosphorous acid when assessing the minimum number of formaldehyde equivalents which we prefer to employ in the starting mixture. Preferably, for efficiency purposes, no more than about 10 equivalents of formaldehyde are added per equivalent of hydroxymethylphosphonic acid (no more than 11 equivalents of formaldehyde per equivalent of phosphorous acid when the hydroxymethylphosphonic acid is formed in situ); most preferably no more than about 3 moles of formaldehyde per mole of hydroxymethylphosphonic acid.

Practice of the invention will become further apparent from the following non-limiting examples.

EXAMPLE I

Hydroxymethylphosphonic acid (100g, 0.89 mol; prepared according to the procedure described in W. R. Griffiths and J. C. Tebby, *Phosphorous*, 6, 223–230(1976) and believed to contain minor amounts of chloromethylphosphonic acid as an impurity) and paraformaldehyde (28g, 0.93mol) were ground together with a mortar and pestle. The resultant mixture was transferred to a flask and maintained under an inert atmosphere of argon. The mixture was then mechanically stirred and heated (using an oil bath) for four hours so as to maintain an internal temperature of 90–95° C., allowing the components to react. As the reaction progressed, a large quantity of the paraformaldehyde was observed to sublime onto the upper parts of the apparatus. The reacted mixture was an amber solution which was cooled and then decanted away from the unreacted paraformaldehyde to give a viscous oil which solidified to a waxy solid on standing. The solid composition was analyzed by carbon-13, phosphorous-31 and proton nuclear magnetic resonance spectroscopy; and found to comprise about 60 weight percent di-(phosphonomethyl) formal and about 35 weight percent hydroxymethylphosphonic acid, with the remainder considered to be principally chloromethylphosphonic acid which was attributable to the impurity of the hydroxymethylphosphonic acid starting material. In other words about 61 percent of the phosphorous was found to be present as di-(phosphonomethyl) formal and about 36 percent of the phosphorous was found to be present as hydroxymethylphosphonic acid.

EXAMPLE II

Hydroxymethylphosphonic acid (448g, 4.0 mole; prepared in accordance with the procedure described in U.K. Patent Specification No. 1,076,244 and believed to contain minor amounts of methoxymethyl phosphonic acid, phosphoric acid, and water present as impurities) and paraformaldehyde (120g, 4.0 mole) were ground together with a mortar and pestle. The resultant mixture was placed in a 2 liter flask equipped with an overhead stirrer and condenser, and maintained under an inert atmosphere of nitrogen. The mixture was heated to 100° C. for three and one-quarter hours, allowing the components to react. The reacted mixture was allowed to cool to room temperature, and was then diluted with 600 ml water. Sodium hydroxide (205g, 5.1 mole) was added to the diluted product, thereby forming a composition comprising a mixture of sodium phosphonate salts. During the sodium hydroxide addition, the product was cooled with a water bath and the rate of addition was controlled so as to maintain a temperature of less than 30° C. Another batch of product solution was produced in a similar manner, and the two compositions were combined to form a single composition. The combined composition was analyzed by phosphorus and proton nuclear magnetic resonance spectroscopy. About 51% of the phosphorous was found to be present as di-(phosphonomethyl) formal; and about 35% of the phosphorous was found to be present as hydroxymethylphosphonic acid. About 11% of the phosphorous was also found to be present as methoxymethylphosphonic acid and about 3% of the phosphorous was also found to be present as phosphoric acid, both of which were attributable to impurities in the hydroxymethylphosphonic acid starting material.

EXAMPLE III

A phosphonate composition comprising a mixture of di-(phosphonomethyl) formal and hydroxymethylphosphonic acid, and prepared in accordance with the process of Example II from 1,042g (9.3 mole) hydroxymethylphosphonic acid, and 289g (9.3 mole) paraformaldehyde, was neutralized with 1,488g of a 50% sodium hydroxide solution (18.6 mole). The neutralized product was analyzed by phosphorous nuclear magnetic resonance spectroscopy. About 43% of the phosphorous was found to be present as the tetrasodium salt of di-(phosphonomethyl) formal; about 40% of the phosphorous was found to be present as the disodium salt of hydroxymethyl phosphonic acid; about 3% of the phosphorous was found to be present as trisodium phosphate. (The components containing the remaining phosphorous were not identified). The neutralized product was allowed to stand for about two weeks at room temperature. During this period a considerable amount of crystals formed in the bottom of the solution. The supernatant was decanted away from the crystals, and the crystals were washed with a small amount of water. The washed crystals were dried first by suction and then overnight in a vacuum oven at 65° C., and 225g of a white solid was obtained. This represented about 15% of the total dissolved solids from the neutralized product mixture. Analysis of the white solid by phosphorous nuclear magnetic resonance spectroscopy showed it to be predominantly the disodium salt of hydroxymethylphosphonic acid, along with approximately 20 mole % trisodium phosphate.

The supernatant from the crystallization was also analyzed by phosphorous nuclear magnetic resonance spectroscopy. About 62% of the phosphorous was found to be present as the tetrasodium salt of di-(phosphonomethyl) formal; about 18% of the phosphorous was found to be present as the disodium salt of hydroxymethyl phosphonic acid; and about 2% of the phosphorous was found to be present as trisodium phosphate, with the components containing the remaining phosphorous being unidentified. It is evident that the crystallization process of this example resulted in a substantial increase in the relative amount of di-(phosphonomethyl) formal (as a sodium salt) present in the supernatant composition and decreases in the relative amounts of hydroxymethylphosphonic acid (as a sodium salt) and phosphate therein.

EXAMPLE IV

Phosphorous acid (1.6g, 20 mmol) and paraformaldehyde (1.5g, 50 mmol) were ground together with a mortar and pestle, and the resulting mixture was transferred to a flask and placed under a nitrogen atmosphere to exclude moisture. The mixture was heated for 3 hours using a 100° C. oil bath, causing the mixture to melt, and allowing its components to react. The reactants were then allowed to cool and to stand overnight at room temperature. They were then reheated for an additional 3 hours using an oil bath at 100° C. The resulting composition was cooled to room temperature and was examined by phosphorous, carbon and proton nuclear magnetic resonance spectroscopy. About 27% of the phosphorous was found to be present as di-(phosphonomethyl) formal; about of the phosphorous was found to be present as hydroxymethylphosphonic acid and about 32% of the phosphorous was found to be present as phosphorous acid.

EXAMPLE V

A sample of hydroxymethylphosphonic acid (215 g, 1.9 mole; prepared in accordance with the procedure described in U. K. Patent Specification No. 1,076,244 and believed to contain about 25g of methoxymethylphosphonic acid, approximately 10g of phosphoric acid and about 25g of water as impurities) was placed in a glass-lined, 2-liter Parr reactor. Formalin solution (174g) containing 64g (2.15 mole) of formaldehyde was added. The resulting solution contained a total 115g water (26% of mixture) and 19g methanol (4% of mixture). The reactor was sealed and heated so as to maintain a temperature of 150–180° C. for a period of forty minutes. The reactor was allowed to cool to room temperature, and the reacted mixture was then stripped at 55° and 20 torr to remove the bulk of the water and methanol. An aliquot of the resulting composition was then removed and examined by phosphorous and proton nuclear magnetic resonance spectroscopy. About 23% of the phosphorous was found to be present as di-(phosphonomethyl) formal; and about 61% of the phosphorous was found to be present as hydroxymethylphosphonic acid. About 11% of the phosphorous was also found to be present as methoxymethylphosphonic acid; and about 5% of the phosphorous was also found to be present as phosphoric acid, both of which were attributable to impurities in the hydroxymethylphosphonic acid starting material.

EXAMPLE VI

Phosphorous acid (5.0g, 61mmol) and formaldehyde (as formalin-37% solution containing 11% methanol; 19.8g, 244 mmol) were heated in a sealed reactor for two hours at 150° C. The reaction product was then cooled, transferred to a flask and concentrated at 60° C and 20–40mm. Examination of the resulting composition by proton and phosphorous-31 nuclear magnetic resonance spectroscopy showed it to contain 45% di-(phosphonomethyl) formal, 50% hydroxymethylphosphonic acid, and 5% of an unknown impurity.

The procedure of reacting phosphorous acid with formaldehyde in solution was repeated several additional times. However the yield of di-(phosphonomethyl) formal achieved in Example VI was not attained again. Accordingly, in order to produce the compositions of the instant invention which have a substantial content of di-(phosphonomethyl) formal we prefer to either form the di-(phosphonomethyl) formal under substantially anhydrous conditions, or to increase the relative amount of di-(phosphonomethyl) formal in the compositions by precipitating out the disodium salt of hydroxymethylphosphonic acid.

The di-(phosphonomethyl) formal is a bis-phosphonic acid polyether which is considered particularly useful as a corrosion inhibitor for aqueous systems. While the di-(phosphonomethyl) formal may also be used in combination with hydroxymethylphosphonic acid for corrosion inhibition, it is desirable to have a ratio of the mole percent of phosphorous present as di-(phosphonomethyl) formal to the mole percent of phosphorous present as hydroxymethylphosphonic acid in the combination of at least about 1:3, most preferably at least about 2:3. Preferably, at least about 25% of the phosphonate groups of the compositions of this invention are present as di-(phosphonomethyl) formal, most preferably at least about 40%.

The utility of compositions comprising di-(phosphonomethyl) formal will become further apparent from the following. A standard corrosive test water solution containing 30 milligrams per liter (mg/1) calcium chloride, 37 mg/1 magnesium sulfate, 100 mg/1 sodium sulfate, 50 mg/1 sodium chloride and 100 mg/1 sodium carbonate was prepared by adding the recited salts to distilled water. The solution was thus free of such materials as chromate, zinc, phosphate, polyphosphate, nitrite, nitrate and borate. The test solution was added to a simulated cooling water test rig having a 12 liter reservoir and a recirculation loop. The rig generally corresponded in design with that described in The Development and Use of Corrosion Inhibitors, A. Marshall and B. Greaves, Oyez, London (1983). Four precleaned and preweighed mild steel metal test coupons were immersed in the test solution within the recirculating loop, and a fifth coupon was immersed in the test solution in the reservoir. The test solution in the rig was maintained at a temperature of about 55° C., and the pH was adjusted to about 8.5 as the test began. The recirculating flow (generally about 9 liters/min) produced a water velocity of approximately 1.6 feet/sec. past the coupons in the recirculation line while the water in the reservoir was substantially quiescent.

Two of the coupons in the recirculation line were removed after only 24 hours, and the remaining coupons were removed after 48 hours. The coupons were cleaned after removal and reweighed to determine weight loss. An average corrosion rate in mils (thousandths of an inch) per year was then calculated for the four recirculation line coupons, and a corrosion rate in mils per year was separately calculated for the reservoir coupon. The corrosion rates for the standard corrosive test water solution were calculated as 186 mils per year for the recirculation line coupons and 72 mils per year for the reservoir coupon.

Additional runs were made using the same procedure except that 30 ppm (runs b and c), 50 ppm (run d), 100 ppm (runs e, f and g) or 200 ppm (runs h and i) of hydroxymethylphosphonic acid ("HMPA") synthesized by conventional means from phosphorous acid and formaldehyde (See U.K. Patent Specification 1,076,244), was added to the standard corrosive test water solution. The corrosion rates for the recirculation line coupons and reservoir coupon were calculated. The percent corrosion inhibition compared to the run using only the standard corrosive test water (run a) is shown in Table A.

A series of 9 runs (runs j through r) was made using a mixture of equal amounts (on a weight basis) of hydroxymethylphosphonic acid (i.e. "HMPA") and di-(phosphonomethyl) formal (i.e. "DPMF") prepared generally in accordance with the procedure illustrated above, as the corrosion inhibitor. The percent corrosion inhibitor using each component at 12.5 ppm (runs j and k), 15 ppm (runs i through p), 20 ppm (run q), and 25 ppm (run r) is shown in Table A.

TABLE A

| Run No. | Corrosion Inhibitor | Total Inhibitor Dosage (ppm) | Percent Reduction in Corrosion Rate | |
|---|---|---|---|---|
| | | | Recirculation Line | Reservoir |
| a | None | 0 | 0 (Base Rate) | 0 (Base Rate) |
| b | HMPA | 30 | 49 | 43 |
| c | HMPA | 30 | 46 | 41 |
| d | HMPA | 50 | 72 | 26 |
| e | HMPA | 100 | 96 | 56 |
| f | HMPA | 100 | 93 | 37 |
| g | HMPA | 100 | 94 | 43 |
| h | HMPA | 200 | 99 | 62 |
| i | HMPA | 200 | 98 | 75 |
| j | DPMF/HMPA (1:1) | 25 | 87 | 35 |
| k | DPMF/HMPA (1:1) | 25 | 87 | 25 |
| l | DPMF/HMPA (1:1) | 30 | 78 | 53 |
| m | DPMF/HMPA (1:1) | 30 | 94 | 4 |
| n | DPMF/HMPA (1:1) | 30 | 98 | 15 |
| o | DPMF/HMPA (1:1) | 30 | 93 | 3 |
| p | DPMF/HMPA (1:1) | 30 | 90 | −3 |
| q | DPMF/HMPA (1:1) | 40 | 99 | 36 |
| r | DPMF/HMPA (1:1) | 50 | 99 | 68 |

The Examples describe particular embodiments of the invention. Other embodiments will become apparent to those skilled in the art from a consideration of the specification or practice of the invention disclosed herein. It is understood that modifications and variations may be produced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A method of preparing phosphonate compositions comprising—a mixture of hydroxymethylphosphonic acid and—di-(phosphonomethyl) formal, comprising the steps of:
   (a) forming an intimate mixture of a first components consisting of hydroxymethylphosphonic acid and a second component selected from the group consisting of formaldehyde and formaldehyde condensates; said intimate mixture having at least about 0.5 equivalents of formaldehyde per equivalent of hydroxymethylphosphonic acid; and
   (b) subjecting the intimate mixture formed in step (a) to a temperature of between about 100° C. and 180° C. for a time sufficient to allow the first and second components to react to form a reacted mixture— wherein at least about 25 mole percent of the phosphonate groups in the phosphonate composition are present as—di-(phosphonomethyl) formal.

2. The method of claim 1 wherein in step (a) the intimate mixture is formed by adding hydroxymethylphosphonic acid and said second component and mixing said first and second components at a temperature below about 80° C.; said intimate mixture having between about 0.5 and 10 equivalents of formaldehyde per equivalent of hydroxymethylphosphonic acid.

3. The method of claim 2 wherein in step (a) the first and second components are intimately mixed by dissolving them in water.

4. The method of claim 3 further comprising the step of adding base to the reacted mixture in an amount sufficient to provide a pH of at least about 7.

5. The method of claim 4 wherein the base is an alkali metal hydroxide.

6. The method of claim 2 wherein in step (a) the first and second components are intimately mixed by mechanically blending them under substantially anhydrous conditions.

7. The method of claim 6 wherein the first and second components are reacted under substantially anhydrous conditions.

8. The method of claim 1 wherein forming an intimate mixture of said first component and said second component includes mixing phosphorous acid with at least one compound selected from the group consisting of formaldehyde and formaldehyde condensates and heating them to a temperature of between about 100° C. and 180° C., thereby forming said first component in situ.

9. The method of claim 8 wherein the intimate mixture of said first component and second component is formed under substantially anhydrous conditions, and said first and second components are reacted under substantially anhydrous conditions.

10. The method of claim 1 wherein the reacted mixture comprises both di-(phosphonomethyl) formal and hydroxymethylphosphonic acid and wherein the proportion of di-(phosphonomethyl) formal therein is enriched relative to the hydroxymethylphosphonic acid therein by adding sufficient amount of sodium hydroxide to an aqueous solution comprising said reacted mixture to form the disodium salt of the hydroxymethylphosphonic acid and the tetrasodium salt of the di-(phosphonomethyl) formal, thereby causing the selective formation of crystals comprising the disodium salt of hydroxymethylphosphonic acid, and then separating said crystals from the supernatant.

11. The method of claim 1 wherein the reaction of the first component with the second component is continued until the ratio of the mole percent, of phosphorous present in the reacted mixture as di-(phosphonomethyl) formal to the mole percent of phosphorous present in the reacted mixture as hydroxymethylphosphonate is at least about 1:3.

12. The method of claim 1 wherein at least about 40 mole percent of the phosphonate groups in the phosphonate composition are present as di-(phosphonomethyl) formal.

13. A phosphonate composition comprising a mixture of hydroxymethylphosphonic acid and di-(phosphonomethyl) formal wherein at least about 25 mole % of the phosphonate groups are present as di-(phosphonomethyl) formal.

14. A phosphonate composition comprising a mixture of hydroxymethylphosphonic acid and di-(phosphonomethyl) formal wherein at least about 40% of the phosphonate groups are present as di-(phosphonomethyl) formal.

15. A phosphonate composition comprising a mixture of hydroxymethylphosphonic acid and di-(phosphonomethyl) formal wherein at least about 25% of the phosphonate groups are present as di-(phosphonomethyl) formal, which is a product of a process comprising the steps of:
   (a) forming a solution of a first component consisting of hydroxymethylphosphonic acid and a second component selected from the group selected from the group consisting of formaldehyde and formaldehyde condensates, including mixing phosphorous acid with at least one compound selected from the group consisting of formaldehyde and formaldehyde condensates and heating them to a temperature of between about 100° C. and 180° C., thereby forming said first component in situ; said solution of first component and second component having at least about 0.5 equivalents of formaldehyde per equivalent of hydroxymethylphosphonic acid;
   (b) subjecting the solution of first and second components formed in step (a) to a temperature of between about 100° C. and 180° C. for a time sufficient to allow the first and second components to react to form a reacted mixture comprising di-(phosphonomethyl) formal and hydroxymethylphosphonic acid; and
   (c) enriching the proportion of di-(phosphonomethyl) formal relative to the hydroxymethylphosphonic acid in an aqueous solution comprising the reacted mixture by adding a sufficient amount of sodium hydroxide thereto to form the disodium salt of hydroxymethylphosphonic acid and the tetrasodium salt of the di-(phosphonomethyl) formal, thereby causing the selective formation of crystals comprising the disodium salt of hydroxymethylphosphonic acid, and then separating said crystals from the supernatant.

16. A phosphonate composition comprising a mixture of hydroxymethylphosphonic acid and di-(phosphonomethyl) formal wherein at least about 25 mole % of the phosphonate groups are present as di-(phosphonomethyl) formal, which is a product of a process comprising the steps of:
(a) forming a solution of a first component consisting of hydroxymethylphosphonic acid and a second component selected from the group consisting of formaldehyde and formaldehyde condensates by dissolving hydroxymethylphosphonic acid and said second component in water, said solution of first and second components having between about 0.5 and 10 equivalents of formaldehyde per equivalent of hydroxymethylphosphonic acid; and
(b) subjecting the solution of first and second components formed in step (a) to a temperature of between about 100° C. and 180° C. for a time sufficient to allow the first and second components to react to form a reacted mixture comprising di-(phosphonomethyl) formal.

17. The phosphonate composition of claim 16 which comprises hydroxymethylphosphonic acid and which is a product of enriching the proportion of di-(phoshponomethyl) formal in a reacted mixture produced by a process including steps (a) and (b) relative to the hydroxymethylphosphonic acid therein by adding a sufficient amount of sodium hydroxide to an aqueous solution comprising said reacted mixture to form the disodium salt of hydroxymethylphosphonic acid and the tetrasodium salt of the di-(phosphonomethyl) formal, thereby causing the selective formation of crystals comprising the disodium salt of hydroxymethylphosphonic acid, and then separating said crystals from the supernatant.

18. A phosphonate composition comprising a mixture of hydroxymethylphosphonic acid and di-(phosphonomethyl) formal wherein at least about 25 mole % of the phosphonate groups are present as di-(phosphonomethyl) formal, which is a product of a process comprising the steps of;
(a) forming a substantially anhydrous intimate mixture of a first component consisting of hydroxymethylphosphonic acid and a second component selected from the group consisting of formaldehyde and formaldehyde condensates, by adding hydroxymethylphosphonic acid component to said second component and mechanically mixing the first and second component at a temperature below about 80° C., said mixture of first and second components having between about 0.5 and 10 equivalents of formaldehyde per equivalent of hydroxymethylphosphonic acid; and
(b) subjecting the intimate mixture of first and second components formed in step (a) to a temperature between about 100° C. and 180° C. under substantially anhydrous conditions for a time sufficient to allow the first and second components to react to form a reacted mixture comprising di-(phosphonomethyl) formal.

19. The phosphonate composition of claim 18 which comprises hydroxymethylphosphonic acid and which is a product of enriching the proportion of di-(phosphonomethyl) formal in a reacted mixture produced by a process including steps (a) and (b) relative to the hydroxymethylphosphonic acid therein by adding a sufficient amount of sodium hydroxide to an aqueous solution comprising said reacted mixture to form the disodium salt of hydroxymethylphosphonic acid and the tetrasodium salt of the di-(phosphonomethyl) formal, thereby causing the selective formation of crystals comprising the sodium salt of hydroxymethylphosphonic acid, and then separating said crystals from the supernatant.

20. A phosphonate composition comprising a mixture of hydroxymethylphosphonic acid and di-(phosphonomethyl) formal wherein at least about 25% of the phosphonate groups are present as di-(phosphonomethyl) formal, which is a product of a process comprising the steps of:
(a) forming a substantially anhydrous intimate mixture of a first component selected from the group consisting of hydroxymethylphosphonic acid and a second component selected from the group consisting of formaldehyde and formaldehyde condensates, including mixing phosphorous acid with at least one compound selected from the group consisting of formaldehyde and formaldehyde condensates and heating them to a temperature of between about 100° C. and 180° C., thereby forming said first component in situ; said mixture of first and second components having at least about 0.5 equivalents of formaldehyde per equivalent of hydroxymethylphosphonic acid and being formed under substantially anhydrous conditions; and
(b) subjecting the intimate mixture of first and second components formed in step (a) to a temperature of between about 100° C. and 180° C. under substantially anhydrous conditions for a time sufficient to allow the first and second components to react to form a reacted mixture comprising di-(phosphonomethyl) formal.

21. The phosphonate composition of claim 20 which comprises hydroxymethylphosphonic acid and which is a product of enriching the proportion of di-(phosphonomethyl) formal in a reacted mixture produced by a process including steps (a) and (b) relative to the hydroxymethylphosphonic acid therein by adding a sufficient amount of sodium hydroxide to an aqueous solution comprising said reacted mixture to form the disodium salt of hydroxymethylphosphonic acid and the tetrasodium salt of the di-(phosphonomethyl) formal, thereby causing the selective formation of crystals comprising the sodium salt of hydroxymethylphosphonic acid, and then separating said crystals from the supernatant.

22. An improved phosphonate composition of the type containing hydroxymethylphosphonic acid, wherein the improvement comprises di-(phosphonomethyl) formal in an amount such that the mole ratio of phosphonate groups present as di-(phosphonomethyl) formal to phosphonate groups present as hydroxymethylphosphonate is at least about 2:3.

23. The improved phosphonate composition of claim 22 wherein at least about 25 mole % of the phosphonate groups are present as di-(phosphonomethyl) formal.

* * * * *